(12) United States Patent
Maitland et al.

(10) Patent No.: US 7,614,673 B2
(45) Date of Patent: Nov. 10, 2009

(54) CONFORMING ARTIFICIAL FINGER MECHANISM

(75) Inventors: Murray E. Maitland, Seattle, WA (US);
M. Jason Highsmith, Tampa, FL (US);
Craig Lusk, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 11/933,806

(22) Filed: Nov. 1, 2007

(65) Prior Publication Data

US 2008/0109084 A1  May 8, 2008

Related U.S. Application Data

(60) Provisional application No. 60/864,066, filed on Nov. 2, 2006.

(51) Int. Cl.
*B25J 15/08* (2006.01)
(52) U.S. Cl. .................................... 294/106; 294/902
(58) Field of Classification Search ................ 294/106, 294/902
See application file for complete search history.

(56) References Cited

U.S. PATENT DOCUMENTS

| | | | | |
|---|---|---|---|---|
| 3,623,617 | A | * | 11/1971 | Nemessanyi ................. 414/640 |
| 4,327,896 | A | * | 5/1982 | Whitehead .................... 254/88 |
| 5,711,565 | A | * | 1/1998 | Smith et al. ................... 294/88 |
| 6,423,099 | B1 | | 7/2002 | Iversen et al. |
| 6,921,419 | B2 | | 7/2005 | Weir et al. |
| 7,370,896 | B2 | * | 5/2008 | Anderson et al. ........... 294/106 |
| 2005/0234564 | A1 | | 10/2005 | Fink et al. |
| 2006/0224249 | A1 | | 10/2006 | Winfrey |

OTHER PUBLICATIONS

Zollo, L et al., Biomechatronic Design and Control of an Anthropomorphic Artificial Hand for Prosthetics and Robotics Application, 2006 1st IEEE RAS & EMBS International Conference on Biomedical Robotics and Biomechatronics. p. 6, Feb. 2006.

Zhao, J. et al., Five Finger Underactuated Prosthetics Hand System, IEEE International Conference on Mechatronics and Automation, p. 1453-1458, Jun. 2006s.

(Continued)

*Primary Examiner*—Paul T Chin
(74) *Attorney, Agent, or Firm*—Ronald E. Smith; Smith & Hopen, P.A.

(57) ABSTRACT

A prosthetic finger includes a crossed four (4) bar linkage system having a base formed by a base bar, two cross bars, and an interface bar that engages an object to be held. The base bar is fixed to an artificial finger of an amputee. A first cross bar has a first end pivotally mounted to a first end of the base bar and a second cross bar has a first end pivotally mounted to a second end of the base bar. The first cross bar has a second end pivotally mounted to a first end of the interface bar and the second cross bar has a second end pivotally mounted to a second end of the interface bar. The first and second cross bars are slideably interconnected to one another at a cross point which changes its location as the prosthesis grasps objects of differing sizes and shapes.

6 Claims, 8 Drawing Sheets

OTHER PUBLICATIONS

Bondhoo, V. et al., Design of an Artificial Muscle Actuated Finger Toward Biomimetic Prosthetic Hand, 2005 12th International IEEE International Conference on Advanced Robotics, pp. 368-345, Jul. 2005.

Schulz, S. et al., A Hydraulically Driven Multifunctional Prosthetic Hand, Robotica (UK), vol. 23, Issue 3, pp. 233-239, May 2005.

Lin et al., Mechanism Design of a New Multifingered Robotic Hand, 1996 IEEE International Conference on Robotics Automation, pp. 1471-1476, Apr. 1996.

Hoshino, K. et al., Pinching Finger Tips in Humanoid Robot Hand, 2005 IEEE International Symposium on Computation Intelligence in Robotics and Automation, pp. 705-712, Jun. 2005.

* cited by examiner

CONFORMING ARTIFICIAL FINGER MECHANISM

CROSS REFERENCE TO RELATED APPLICATION

This application claims priority to U.S. Provisional Patent Application No. 60/864,066, entitled "Conforming Artificial Finger Mechanism for Prosthetic or Robotic Hands", filed on Nov. 2, 2006, the contents of which are herein incorporated by reference.

STATEMENT OF GOVERNMENT INTEREST

This invention was made with U.S. government support under Grant No. 6140100000 awarded by the U.S. Department of Education/RSA. The government has certain rights in the invention.

BACKGROUND OF THE INVENTION

1. Field of the Invention

This invention relates to prosthetics. More particularly, it relates to a non-anatomical artificial finger or fingertip that does not require complex control systems.

2. Description of the Prior Art

Most upper extremity amputations are the result of abnormal development, trauma, or medical treatment. Amputations of the hand result in chronic disability. Conventional designs of artificial hands do not perform well at grasping different shapes and sizes of objects. Depending on the design, conventional artificial hands may need complex control systems to coordinate the articulations.

Thus there is a need for an alternate mechanism that improves upon hooks and other forms of non-anatomical prosthetic hands. Current designs of myoelectric devices will also benefit from mechanical adaptations to make them more versatile and functional.

U.S. patent application No. 0234564, entitled Enhanced-Functionality Prosthetic Limb, filed Oct. 20, 2005 by Fink et al, discloses an enhanced functionality prosthetic hand or gripping device and fore arm which is manually or motor powered, intended primarily for pediatric use. The inventive structure is attached to the residual arm of a below-elbow or an above-elbow amputee. The device is expandable in length or size to accommodate child growth and it includes grasp locking and individual finger locking capability. It provides a wrist joint having three degrees of freedom, dynamic tensional rotation control of wrist, dynamic grasp control to allow grasping of irregular objects, extended grasp for gripping larger objects, excessive force breakaway, and algorithms that facilitate use and adjustment of the prosthesis by the user or care-provider.

U.S. patent application No. 022429, entitled Prosthetic Hand Having A Conformable, Compliant, Grip And Opposable, Functional Thumb, filed Oct. 5, 2006 by Winfrey discloses an anthropomorphic artificial hand having a mechanical system that allows the digits to be compliant to pressure that tends to flex the digits and provides for the digits to be self-biasing to conform to the shape of the object being grasped. The hand includes one to four fingers, with the fingers having up to three joints each. The hand may also include a thumb that can be rotated into and out of the opposition to the fingers. The joints of the thumbs are also self-biasing to allow conformance to the object being grasped. This allows the hand to use two cables to operate if body powered (one for the fingers, one for the thumb). The hand may also be electronically powered using two channels for operating the fingers and thumb simultaneously.

U.S. Pat. No. 6,423,099, entitled Safety Clutch For A Prosthetic Grip, filed Jul. 23, 2002 by Iversen, discloses a grip for an artificial or prosthetic arm. The novel structure includes at least two opposable digits and a drive linkage powered by a drive motor. When the drive motor is powered it enables the two opposable digits to grip. The drive linkage includes a drive and transmissions attached to the drive motor. A blacklock is connected to the drive and transmission. Surrounding the black-lock is a blacklock housing containing a drive, selected transmission elements, and the blacklock. A stop element is also included for holding the blacklock housing fixed with respect to ground. The stop element can be released to allow the blacklock housing to move freely and to avoid power transmission without disrupting the operating structure of the transmission.

U.S. patent application No. 0117034, entitled Externally-Powered Hand Prosthesis, filed Jun. 17, 2004 by Weir et al., discloses an externally-powered prosthesis mechanism usable with persons with amputations at or proximal to the level of the metacarpophalangeal joint, as well as persons with high-level amputations. The prosthesis mechanism includes a grasping mechanism including a mechanically operable thumb member kinematically linked to the finger member such that the grasping mechanism is disposed in respective opened and closed configurations when the finger member is respectively moved away from and toward the thumb member. The prosthesis mechanism further includes a drive system extending tangentially with respect to the grasping mechanism and includes a motor operatively connected to drive at least one planetary gear stage, which is operatively connected to drive the grasping mechanism to the opened configuration when the motor is driven in a first direction and further drive the grasping mechanism to the closed configuration when the motor is driven in a second opposite direction.

A paper entitled Biomechatronic Design and Control of an Anthropomorphic Artificial Hand For Prosthetics And Robotics Application, published in a journal entitled: IEEE RAS & EMBS International Conference on Biomedical Robotics and Biomechatronics, in February 2006 by Zollo et al., discloses a biomechatronic approach to the design of an anthropomorphic artificial hand. The hand is conceived to be applied to prosthetics and biomedical robotics; hence, anthropomorphism is a fundamental requirement to be addressed both in the physical aspect and in the functional behavior. Regarding the hand mechanics, a cable-driven underactuation is provided to lighten the structure, allow anthropomorphic self-adaptation to the object to be grasped, and simplify the control. Two simple PD control systems are formulated and evaluated in a common task of grasping a cylindrical object. The reference input for the control is derived from data on human subjects performing the same task and extracted by the literature. The paper reports simulation results about the comparison with the human case when both control systems are used to close the fingers, so to derive specific indications for the improvement of the hand design.

A paper entitled "Five Finger Underactuated Prosthetics Hand System," published June 2006 in the IEEE International Conference on Mechatronics and Automation, discloses a five-fingered underactuated prosthetic hand controlled by surface EMG (electromyographic) signals. The prosthetic hand is designed with simplicity, lightweight and dexterity on the requirement of anthropomorphic hands. Underactuated self-adaptive theory is adopted to decrease the number of motors and weight. The fingers of the hand with multi phalanges have the same size as an adult hand. The prosthetic hand control part is based on an EMG motion pattern classifier which combines VLR (variable learning rate) based neural network with wavelet transform and sample entropy. This motion pattern classifier can successfully identify the flexion and extension of the thumb, the index finger and the middle finger, by measuring the EMG signals through three electrodes mounted on the flexor digitorum profundus, flexor pollicis longus and extensor digitorum. Furthermore, via continuously controlling single finger's motion, the five-fingered underactuated prosthetic hand can achieve more prehensile postures such as power grasp. The experimental results show that the system has a great application value.

A paper entitled: "Design of an Artificial Muscle Actuated Finger Towards Biomimetic Prosthetic Hand" was published July 2005 in the 12$^{th}$ International IEEE International Conference on Advance Robotics. This paper discloses the design and modeling of a prosthetic finger for children. Conventional prosthetic hands are simple grippers that restore only the very basic grasping capabilities of the human hand. This paper proposes a biomimetic approach to prosthetic hand design. The musculoskeletal characteristics of the human hand are studied to extract elements that are essential in the design of a biomechanically accurate hand. A four (4) DOF finger design closely mimics the size and kinematics of the human finger. SMA-driven tendon wires are directly attached to the finger structure, in a manner similar to the natural tendons and muscles.

A paper entitled: "A hydraulically driven multifunctional prosthetic hand" was published May 2005 in Robotica (UK), Volume 23, Issue 3. A new prosthetic hand is presented that closely approximate the grasping abilities of a human hand. A large variety of different objects can be grasped reliably and the movements of the hand appear to be natural. This five-finger hand has 15 degrees of freedom driven by small sized flexible fluidic actuators. The drives are within the fingers allowing a very compact and lightweight hand.

Another paper, entitled "Mechanism Design of a New Multifingered Robotic Hand" was published April 1996 in the IEEE International Conference on Robotics Automation. It discloses a new-finger robot hand (NTU hand) with seventeen degrees of freedom (DOF). In contrast to traditional tendon-driven robots, the NTU hand has an uncoupled configuration so that each finger and joint is individually driven. All actuators, mechanical parts and sensors are packed on the human hand. Such compact design makes the hand easily adapt to industrial robot arm and prosthetic applications.

A paper entitled: "Pinching Finger Tips in Humanoid Robot Hand" was published June 2005 in the 2005 IEEE International Symposium on Computation Intelligence in Robotics and Automation. A small-sized and light-weight robotic hand is designed according to the concept of extracting required minimum motor functions and implementing them to the robot. A robot hand is capable of properly realizing a pinching motion with finger tips, by adding the minimum required degree of supplementary freedom which can be realized only with a machine.

In view of the art considered as a whole at the time the present invention was made, it was not obvious to those of ordinary skill in this art how the art could be further advanced.

SUMMARY OF INVENTION

The long-standing but heretofore unfulfilled need for a prosthesis that performs the function of natural fingers is now provided by a new, useful, and nonobvious invention.

The novel conforming artificial finger mechanism includes a base bar, an interface bar, and a cross bar linkage that interconnects the base bar and the interface bar.

The cross bar linkage includes a first cross bar and a second cross bar.

The interface bar is adapted to contact an object to be articulated by the mechanism and preferably has a high friction surface. The interface bar is adapted to rotate about an axis defined by a sliding, non-physical intersection of the first and second cross bars. That axis is also known as moving cross point 20; it is a conceptual, non-physical point. Movement of said conceptual cross point or axis is illustrated in FIGS. 1-5 and 10-15.

The first and second cross bars are coupled to the interface bar and the base bar by uniplanar, hinged joints.

A mechanical bias returns the mechanism to a position of repose upon disengaging from the object.

The novel apparatus accomplishes several goals for the amputee. The primary objective of the invention is to achieve versatility in the shapes and sizes of objects that can be grasped. The novel finger/finger tip offers several unique features: self-positioning mechanisms, increased surface contact between the finger tips and the object surface, less energy required to power the gripping mechanism, decreased control systems required, stability of the object-finger interface over a wide range of motion, lateral stability during grasp and lifting, a predictable interface for sensors and control, efficiency in use and training, more visually acceptable compared to the hook prostheses (after surface structure), and a modular construction that can be accommodated to a wide range of prosthetic designs.

These and other important objects, advantages, and features of the invention will become clear as this description proceeds.

The invention accordingly comprises the features of construction, combination of elements, and arrangement of parts that will be exemplified in the description set forth hereinafter and the scope of the invention is indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
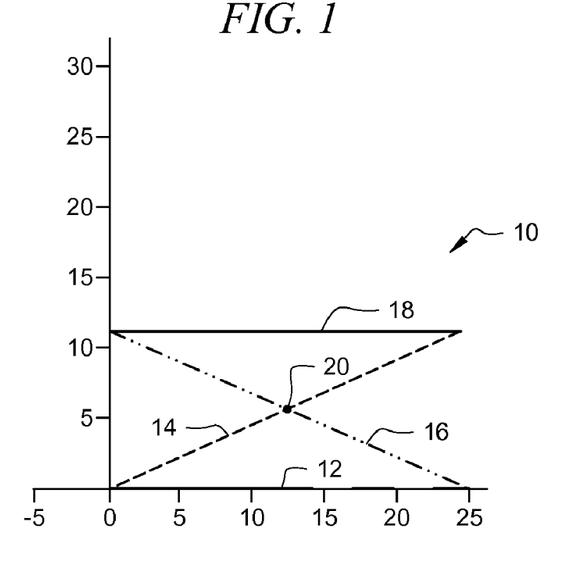
FIG. 1 is a diagrammatic view of the novel four (4) bar linkage system when the object-engaging surface is horizontally disposed.

Referring now to FIG. 1, it will there be seen that the novel structure is denoted diagrammatically as a whole by the reference numeral 10. It includes a crossed four (4) bar linkage system having a base formed by base bar 12, two cross bars 14 and 16, and an interface bar 18. Base bar 12 is affixed to an artificial finger of an amputee. It may be adapted to be attached to various prosthetic devices for finger, hand, forearm, and transhumeral (arm) amputations.

Cross bar 14 has a first end pivotally mounted to a first end of base bar 12 and cross bar 16 has a first end pivotally mounted to a second end of said base bar 12. Cross bar 14 has a second end pivotally mounted to a second end of interface bar 18 and cross bar 16 has a second end pivotally mounted to a first end of said interface bar 18. The pivot points are defined by simple, uniplanar, hinge joints. In the simplest cases the finger may not have intermediate articulations.

As indicated by FIGS. 1-5, the novel prosthesis is used to grasp objects of differing sizes and shapes. Moving cross point 20 is not an articulation, but it is used in mathematical equations. Four (4) bar mechanism 10 replaces the finger pulp in the anatomical sense.

The geometry of each individual 4-bar linkage system is calculated using kinematic equations and estimates from kinesiology. The total range of motion of the object/linkage interface was chosen to be ninety (90) degrees. Using kinematic equations and an iterative process, the ratios of the linkages were calculated so that the linkage would be mechanically obstructed at forty-five (45) degrees (FIG. 2) in either direction of rotation from the preferred resting or in repose position depicted in FIG. 1 where base bar 12 is parallel to interface bar 18 or parallel to the base. The calculated ratio for the bars 12, 14, 16, and 18 is 25:27:27:24 respectively. The ratio may be varied depending on the range of motion and other variables desired.

Figure 2:
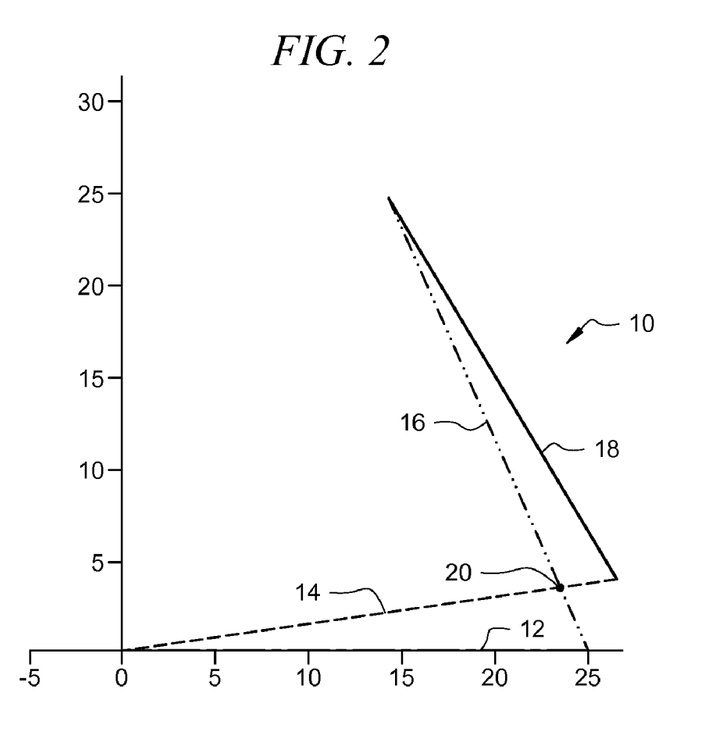
FIG. 2 is a diagrammatic view of the novel linkage system when the object-engaging surface is disposed at an angle of approximately forty-five degrees relative to the horizontal position of FIG. 1 for the purpose of engaging an object positioned to the right of the system as drawn.

FIG. 2 depicts the extreme position required for interface bar 18 to reach forty-five (45) degrees relative to base bar 12. Material dimensions were considered in the calculations.

Figure 3:
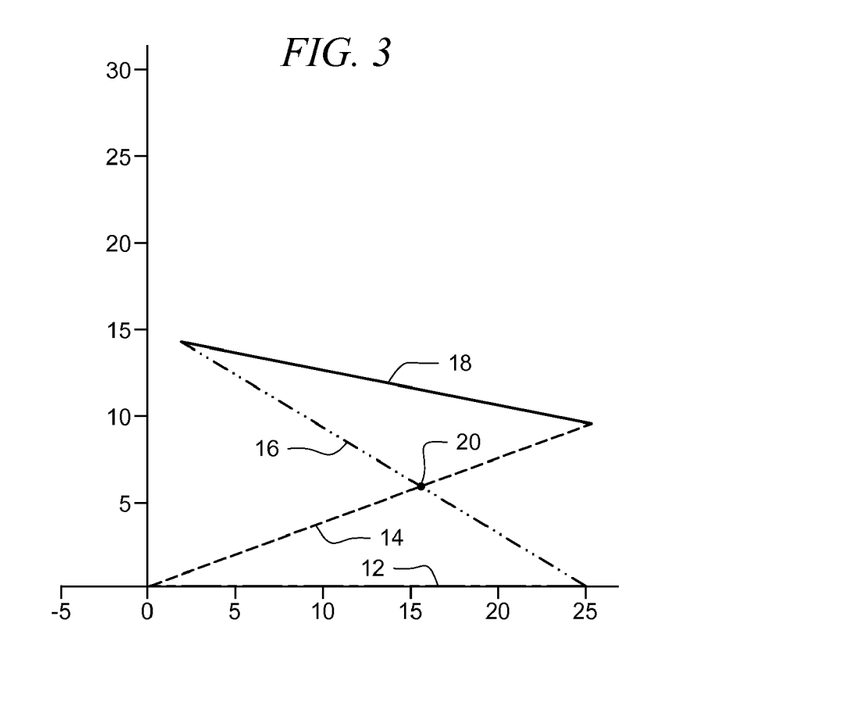
FIG. 3 is a diagrammatic view of the novel linkage system when the object-engaging surface is disposed at an angle of approximately ten degrees relative to the horizontal position of FIG. 1 for the purpose of engaging an object positioned to the right of the system as drawn.

FIG. 3 depicts a less extreme position.

Figure 4:
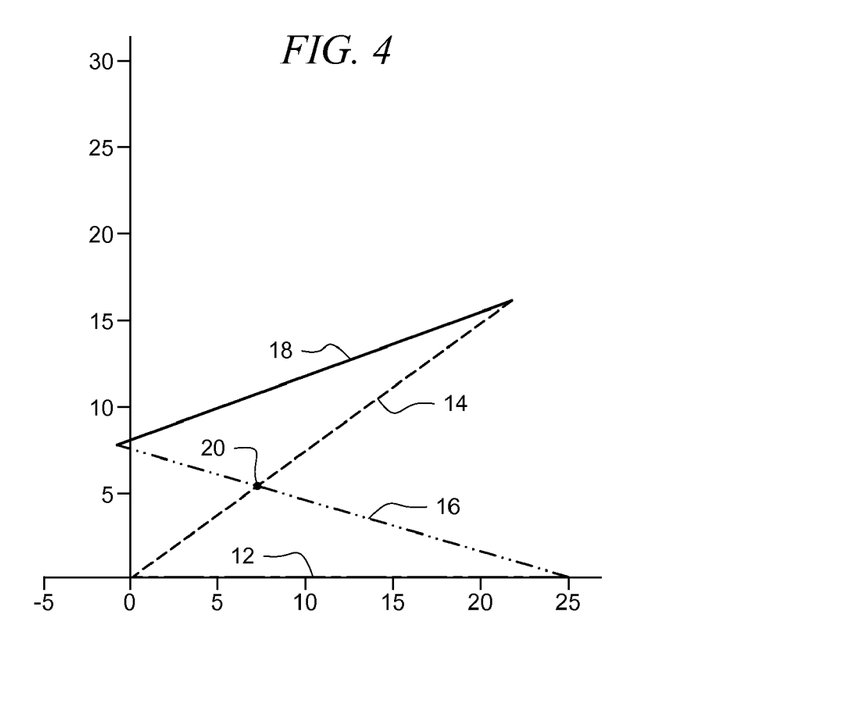
FIG. 4 is a diagrammatic view of the novel linkage system when the object-engaging surface is disposed at an angle of approximately twenty degrees relative to the horizontal position of FIG. 1 for the purpose of engaging an object positioned to the left of the system as drawn.

FIG. 4 depicts a typical orientation in a second direction opposite to the first direction of FIG. 2B.

Figure 5:
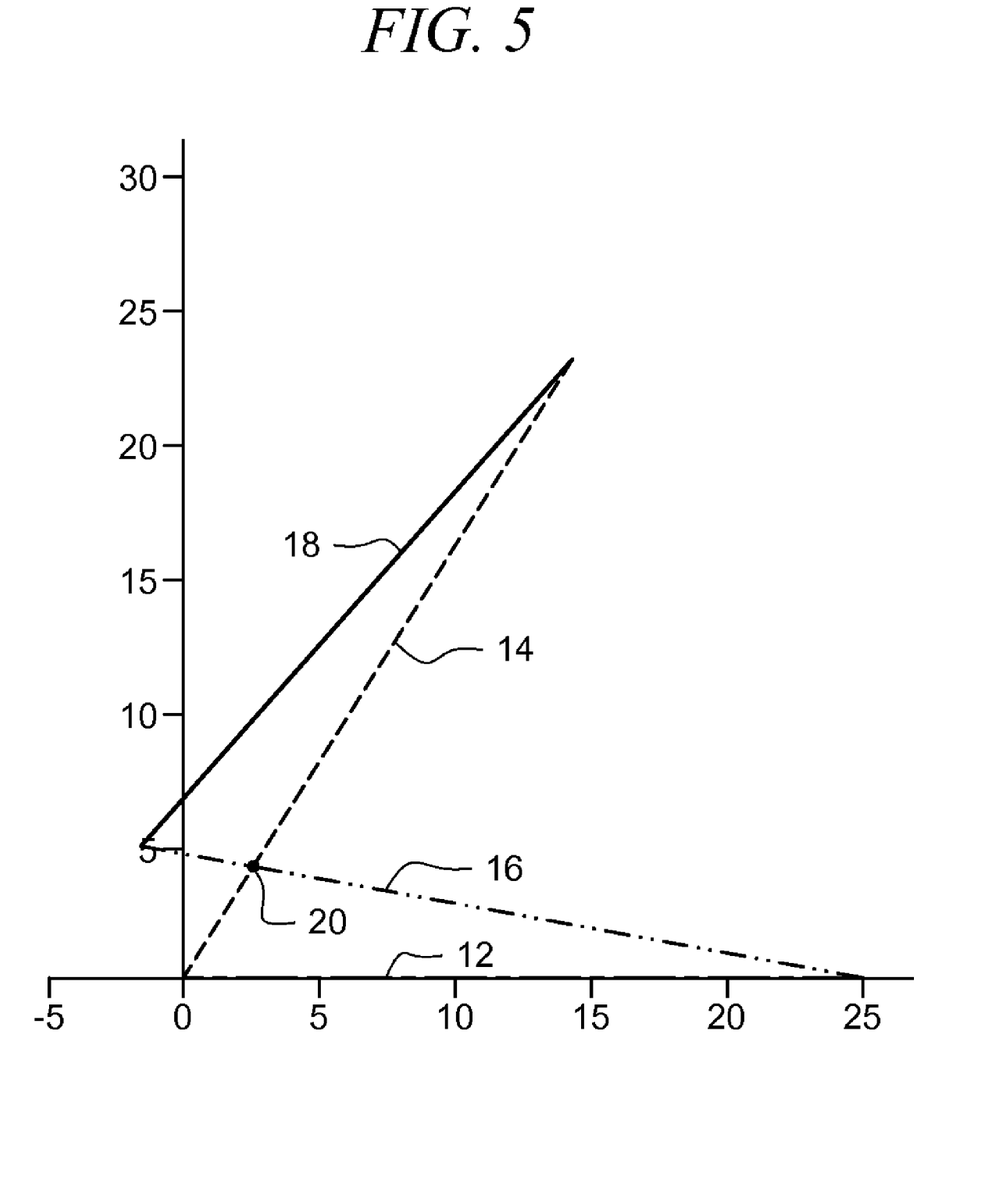
FIG. 5 is a diagrammatic view of the novel linkage system when the object-engaging surface is disposed at an angle of approximately forty-five degrees relative to the horizontal position of FIG. 1 for the purpose of engaging an object positioned to the left of the system as drawn.

FIG. 5 depicts the extreme position in the second direction orientation.

Figure 6:
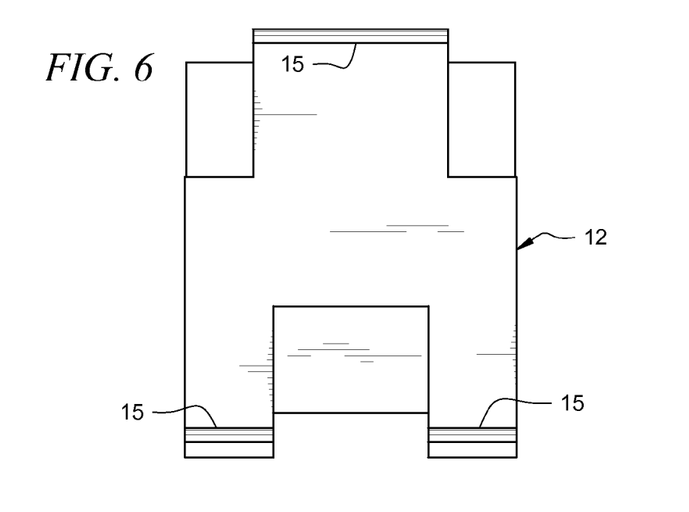
FIG. 6 is a plan view of the base bar.

As indicated in the plan view of FIG. 6, base bar 12 is designed to prevent twisting and lateral bending. A pin at each end of base bar 12 provides a hinge joint for connecting said ends of base bar 12 to the respective first ends of cross bars 14 and 16.

Figure 7:
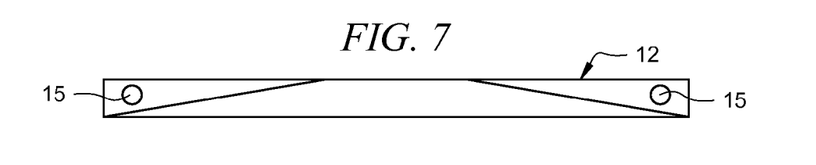
FIG. 7 is a side elevational view of said base bar.

Base bar 12 is depicted in side elevation in FIG. 7.

Figure 8:
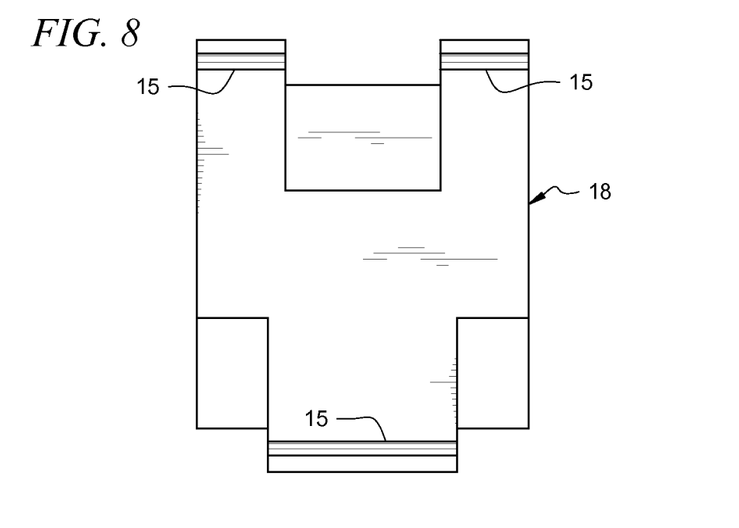
FIG. 8 is a plan view of the top bar.
Figure 9:
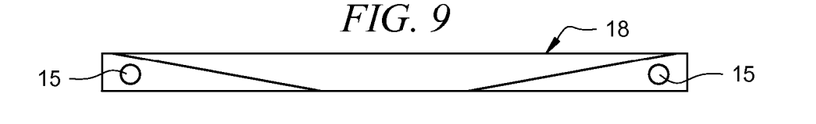
FIG. 9 is a side elevational view of the top bar.

Interface bar 18 is depicted in plan view in FIG. 8 and in side elevation in FIG. 9.

Figure 10:
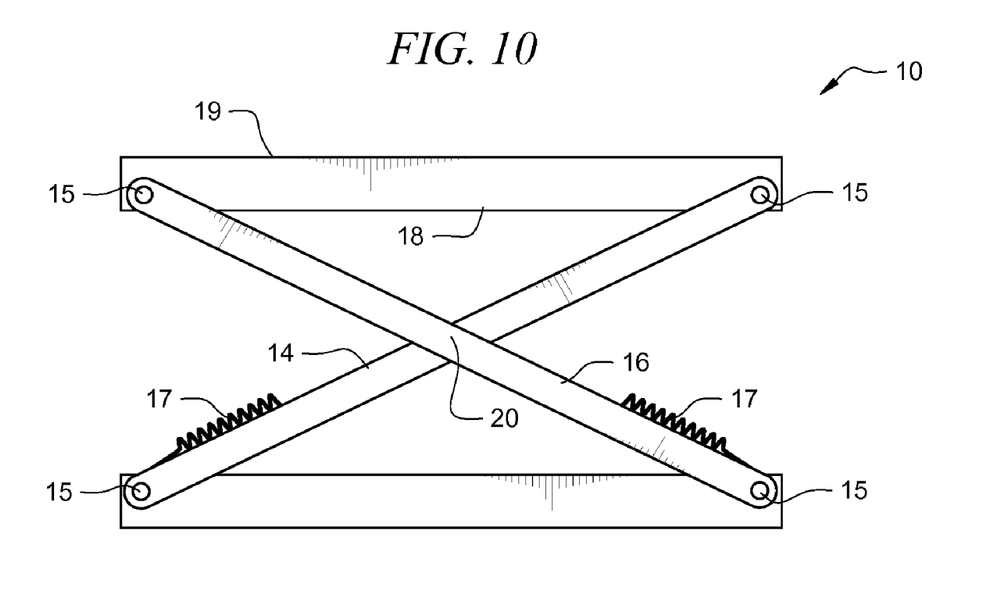
FIG. 10 is a side elevational view of the novel four bar system when in the position diagrammatically depicted in FIG. 1.

FIG. 10 depicts the novel structure 10 when in the position diagrammatically depicted in FIG. 1. A high friction surface 19 overlies interface bar 18. The pins that form the hinge joints for the opposite ends of cross bars 14, 16 are collectively denoted 15. Elongate springs, collectively denoted 17, are mounted to said cross bars as depicted. They provide a bias that returns the structure to a position of repose after contact with an object has ended or they may be adapted to perform other functions. They may also be eliminated in some embodiments.

Figure 11:
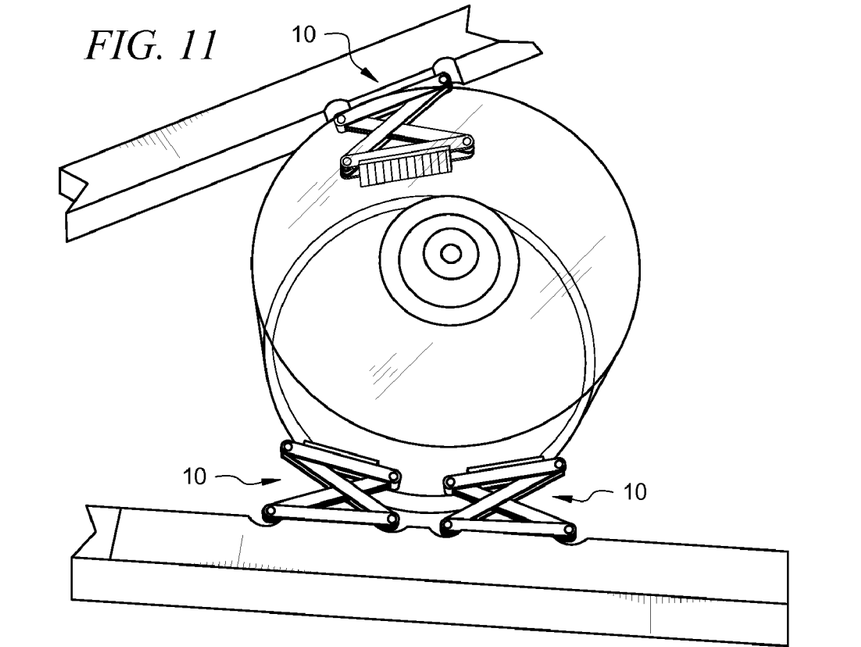
FIG. 11 is a perspective view depicting a large cylindrical object grasped by three (3) of the novel four bar systems.

FIG. 11 depicts the novel structure when gripping a large cylindrical object. There are two (2) prosthetic fingers positioned adjacent one another on the bottom of the object in opposition to one (1) prosthetic finger on the top of the object. This arrangement could be reversed. Moreover, it is understood that the number of prosthetic fingers may be increased or decreased. For example, depending upon the application, there can be one or more prosthetic fingers 10 positioned on a first side of an object to be gripped and one or more prosthetic fingers 10 positioned on an opposite side thereof.

Figure 12:
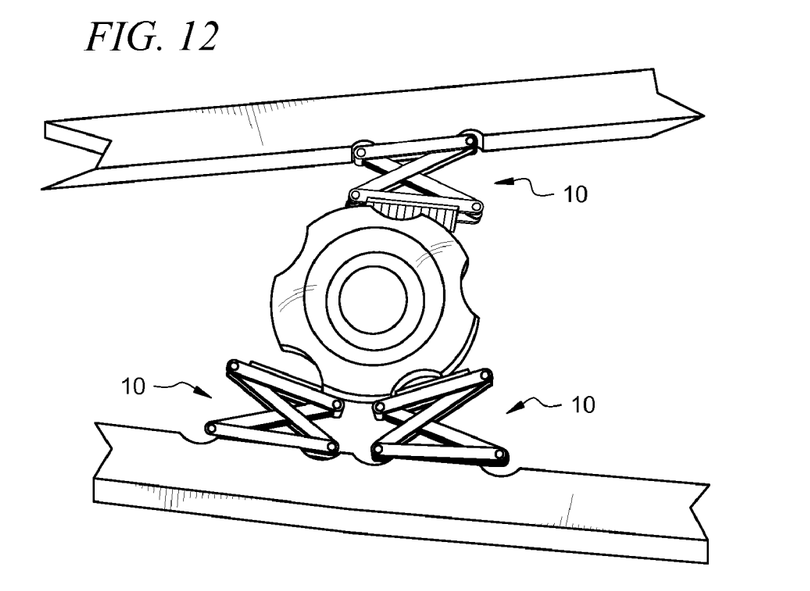
FIG. 12 is a perspective view depicting a cylindrical object grasped by three (3) of the novel four bar systems, said circular object having a smaller diameter than the object depicted in FIG. 11.

FIG. 12 depicts the novel structure when gripping a cylindrical object that is not as large in diameter as the FIG. 11 object. There are two (2) prosthetic fingers positioned adjacent one another on the bottom of the object in opposition to one (1) prosthetic finger on the top of the object in this illustrative example.

When in contact with a cylinder, the four (4)-bar linkage rotates to positions of static equilibrium depending on the direction and the point of application. The geometry of the four (4)-bar linkage system is calculated using kinematic equations for a prototype to achieve a surface range of motion of ninety (90) degrees. The novel apparatus minimizes transverse and lateral rotations by using parallel bars. The preferred object-finger surface is a high friction material used for clinical applications.

Figure 13:
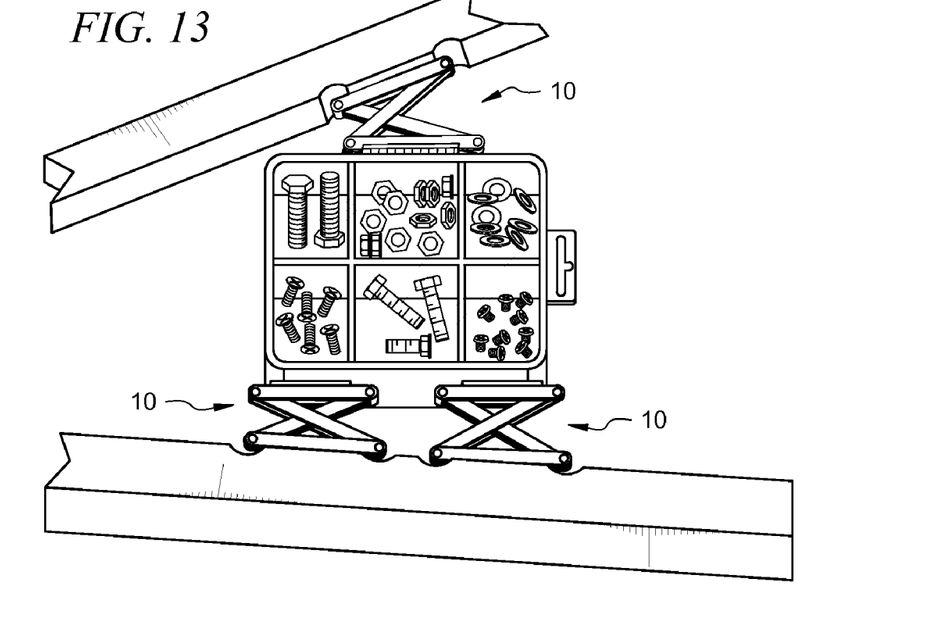
FIG. 13 is a perspective view depicting a rectangular object grasped by three (3) of the novel four bar systems.

FIG. 13 depicts the novel structure when gripping a large rectangular object. There are two (2) prosthetic fingers positioned adjacent one another on the bottom of the object in opposition to one (1) prosthetic finger on the top of the object in this illustrative example.

When in contact with an object that is rectangular in cross section, the novel linkage interface rotates to the object's surface and then, when the top bar is prevented from rotation, the four (4)-bar linkage acts like a stable trestle. Moreover, the four (4)-bar linkage system has positions of static equilibrium that occur in a predictable manner though a wide range of positions.

Figure 14:
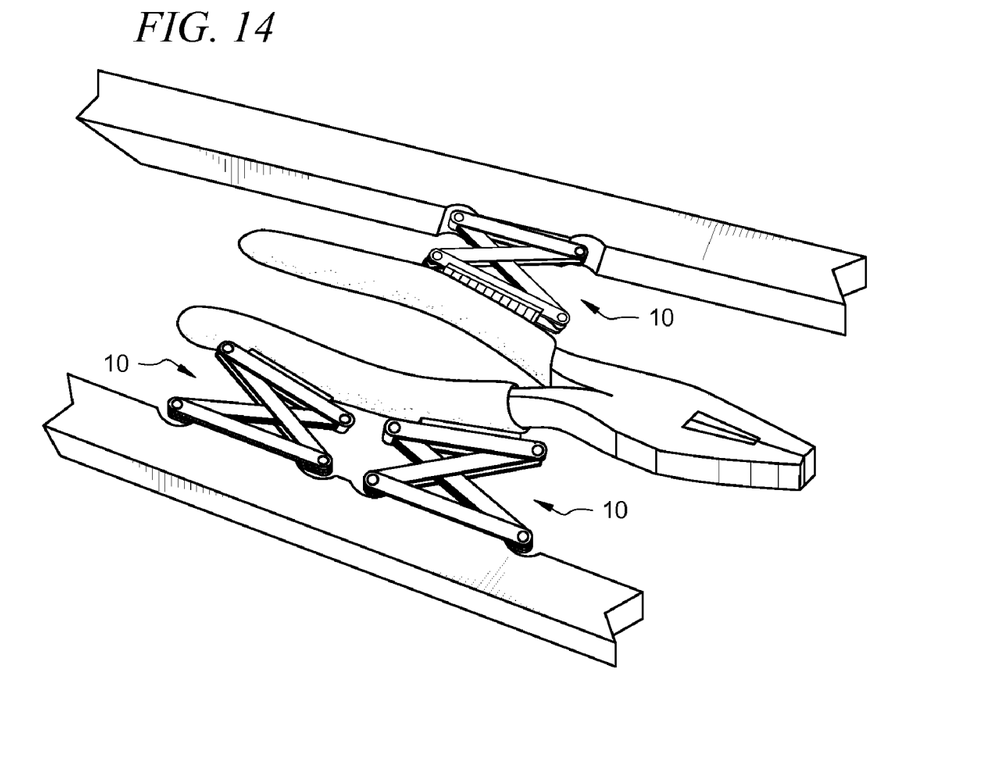
FIG. 14 is a perspective view depicting an object of irregular shape grasped by three (3) of the novel four bar systems.

FIG. 14 depicts novel structure 10 when gripping an object of irregular shape. In this particular example, the object of irregular shape is a pair of pliers.

Figure 15:
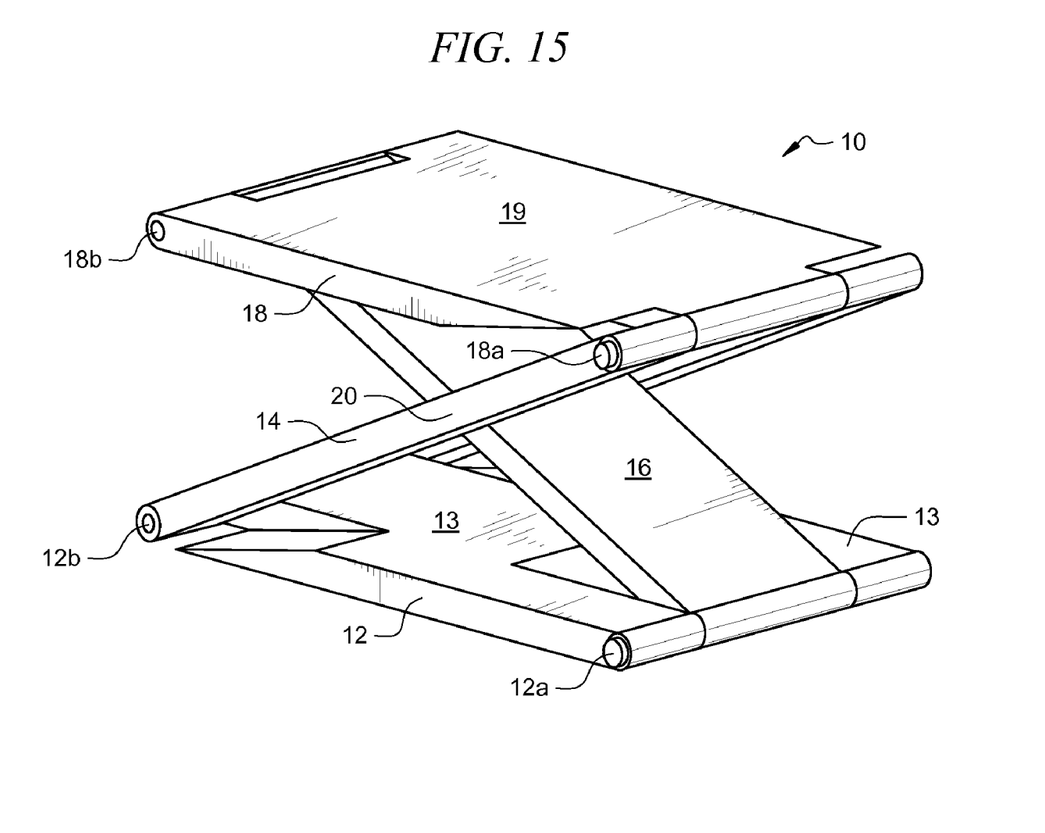
FIG. 15 is a perspective view of the novel four bar system.

FIG. 15 depicts novel structure 10 in perspective. The four bars 12, 14, 16, and 18 are understood from FIG. 15 to be capable of assembly in many different ways, depending upon the application. In the assembly of FIG. 15, base bar 12 is defined by a material 13 that loops around opposite ends of transversely disposed bars 12*a*, 12*b*. Interface bar 18 is defined by a material 19 that loops about respective midsections of transversely disposed bars 18*a*, 18*b*. Cross bar 14 is defined by a material having a first end looped about bar 12*b* and a second end looped about bar 18*a*. Cross bar 16 is defined by a material having a first end looped about bar 12a and a second end looped about bar 18b.

The depicted embodiments are prototypes. Accordingly it is understood that a commercial embodiment of structure 10 will have a decreased size or profile relative to the residual finger. FIG. 15 is also somewhat misleading to the extent that it does not accurately depict bars 12b and 18b and how the respective materials wrap around them but from the drawing as a whole it can be induced as to what a corrected drawing would show. Moreover, the term "materials" should be broadly construed to mean both rigid or flexible materials.

The novel four (4)-bar linkage system is a single degree of freedom mechanism. Knee anatomy has been likened to a crossed four (4)-bar linkage system and such a four (4)-bar linkage has advantages for a fingertip system as well. Advantageously, the position of a single articulation or bar relative to the base determines the position of all of the articulations and bars.

To perform activities of daily living and interact with their environment, people reach out to touch, grasp or manipulate objects with their hands. On a day to day basis, the human hand performs a multitude of functions that vary in complexity and skill. About 100,000 people in the US are living with upper extremity amputations. The amputation can be the result of trauma, fetal developmental anomalies, surgical treatment of cancer, or other medical problems. The hand is exposed to injury that can result in traumatic amputation or mutilation. In combat situations, the torso may be protected by armor but the extremities are susceptible to explosions. Combat soldiers undergo amputation of feet, hands, arms or legs, and in many cases, amputation involves multiple limbs.

Artificial hands are intended to replace those that have been amputated, or were never formed, with a functional device. The mechanical devices become extensions of the person's residual limb. The new finger/fingertip device has several advantages over prosthetic hands heretofore known. In addition, severely disabled individuals require reliable, versatile robotic arms. Finally, there are many manipulative devices that are used in surgical instruments, robots, and mechanical arms.

The novel structure is versatile. The finger/finger tip mechanism grasps and maintains the orientation of a wide range of object shapes and sizes. Conventional artificial hands tend to have a limited range of motion or grasp function, but the novel mechanism conforms to the object surface and shape.

Self-positioning mechanisms passively move the contact surface about an axis of rotation. The structure has forty-five (45) degrees of motion in each direction before the mechanism is physically stopped. The contact surface moves to a position that is advantageous to grasping the object. A myoelectric hand or hook requires precise positioning to grasp an object. The novel structure accommodates to a larger degree of variation in a person's grasp.

The novel structure also provides increased surface contact between the finger tips and the object surface.

Depending on the shape and size of the object, interface bar 18 (or material 19) rotates to conform to the object's surface. Contact with a rectangular object, for example, that is larger than finger tip interface bar 18 and at an angle of less than forty-five (45) degrees from the surface bar, causes the interface bar or material to rotate to the angle of the object's surface. For certain objects the self-positioning finger tips presents the maximal surface area to contact with the object's surface. Increasing the surface area in contact with the object improves the coefficient of friction thus decreasing the force required to prevent slippage. A conventional artificial hand grasps an object in two (2) or three (3) relatively small areas or points of contact. Due to the limited contact with the object, such prior art mechanical hand requires more force and the precision required in the placement of the contact is critical. Some objects require more delicate manipulation, and the distribution of grip forces becomes more important. Lifting a paper cup filled with water is an example were high pressures may cause the cup to deform.

The novel structure also requires less energy to power the gripping mechanism.

Less force is applied because of the larger surface areas in contact with the object being grasped. This translates into a lower energy requirement to produce the force required to grasp and hold the object. This also produces less fatigue for the user or smaller, lighter batteries for myoelectric systems.

Decreased control systems required in the novel structure. An anatomical human finger has the metacarpophalageal joint and two interphalangeal joints resulting in three sagittal plane articulations. Each articulation has a set of muscles to specifically control the sagittal plane position (superficial finger flexors, deep finger flexors, lumbricals, extensor digitorum, extensor indicis and extensor digiti minimi). The novel fingertip mechanism can partly take the place of these anatomical joints. In comparison to artificial hands that have multiple active articulations, passive positioning of the contact surface while active controlling grasp diameter reduces the need for multiple articular controls. A simple body-powered opening device may suffice for many applications.

The inventive structure further provides stability over a wide range of motion. The novel four-bar system allows a self-positioning stable platform since the resultant force passes through the center of rotation for the linkage system. This mechanism is very different compared to hinges or other systems with a fixed center of rotation since these articular approaches tend to be unstable with various loads because of the resultant torque on the structure.

The novel structure also exhibits lateral stability during grasping and lifting. Lateral and vertical stiffness prevent deformity of the system under load. This maintains a consistent friction force and position compared to other conforming approaches.

Sensors and controls are reduced by the novel structure. Conformance is a critical property when a tactile sensory system is embedded on the skin. A passive articulating system with one (1) degree of freedom at the contact interface requires fewer sensory feedback systems for appropriate positioning.

The novel structure is efficient. Its passive grasp system is more functional and easier to use than conventional devices. Accordingly, it is easier to train people to use it.

The novel structure is more visually acceptable compared to the well-known hook prostheses. Conventional prostheses may or may not address the look of the hand in comparison to a human hand. The hook prosthesis is perhaps the least like a natural hand, and there are devices that appear quite real. The present disclosure does not address the cosmetics and acceptability of this new device for the amputee although these are important features. Since the novel device is scalable, and has some geometric flexibility, adequate cosmetic design might be achieved by creating a more anatomically looking finger. This does not necessarily need to have articulations. The rigid substructure could support gel, fabric or other material that would be primarily to fulfill the cosmetic needs.

The novel structure may be integrated into other designs. The novel fingertip design could be modular so that it accommodates a wide range of prosthetic designs.

Versatility, function and cosmetics are goals for artificial hands that can improve the quality of life for people with upper extremity amputations. The novel finger tip device has been shown to grasp a variety of shapes and sizes. Side-by-side comparison followed by improvements in design may allow this unique design to be integrated into different forms of prostheses. The new finger tip mechanism will grasp and maintain the orientation of significantly more objects compared to the myoelectric, hook and system hands. Robotic hands will benefit from this mechanism when versatility is required.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A conforming artificial finger four-bar linkage system, comprising:
   a base bar;
   an interface bar;
   a cross bar linkage that interconnects said base bar and said interface bar;
   said cross bar linkage including a first cross bar and a second cross bar;
   said interface bar adapted to contact an object to be articulated by the four-bar linkage system;
   said first cross bar having a first end pivotally mounted to a first end of said base bar and a second end pivotally mounted to a second end of said interface bar;
   said second cross bar having a first end pivotally mounted to a second end of said base bar and a second end pivotally mounted to a first end of said interface bar; and
   said interface bar adapted to rotate about an axis defined by a non-physical intersection of said first and second cross bars.

2. The four-bar linkage system of claim 1, further comprising:
   said first and second cross bars being coupled to said interface bar and said base bar by uniplanar, hinged joints.

3. The four-bar linkage system of claim 1, further comprising:
   said interface bar having a high-friction surface.

4. The four-bar linkage system of claim 1, further comprising:
   a mechanical bias for returning the four-bar linkage system to a position of repose upon disengaging from said object.

5. A conforming artificial finger four-bar linkage system, comprising:
   a base bar pivotally coupled to an interface bar by a crossed bar linkage that includes a first cross bar and a second cross bar, said interface bar adapted to contact an object to be articulated by the four-bar linkage system and said interface bar adapted to rotate about an axis defined by a non-physical intersection of said first and second cross bars;
   said base bar, said first cross bar, said second cross bar, and said interface bar having predetermined lengths that are related to one another by a ratio of 25:27:27:24, respectively.

6. The four-bar linkage system of claim 1, further comprising:
   said base bar, said first cross bar, said second cross bar, and said interface bar having predetermined lengths that are related to one another by a ratio of 25:27:27:24, respectively.

* * * * *